(12) United States Patent
Chang

(10) Patent No.: US 9,903,807 B2
(45) Date of Patent: Feb. 27, 2018

(54) WEARABLE DEVICE FOR TESTING BIOLOGICAL INFORMATION OF USER AND TESTING SYSTEM HAVING THE SAME

(71) Applicant: HON HAI PRECISION INDUSTRY CO., LTD., New Taipei (TW)

(72) Inventor: Jen-Tsorng Chang, New Taipei (TW)

(73) Assignee: HON HAI PRECISION INDUSTRY CO., LTD., New Taipei (TW)

(*) Notice: Subject to any disclaimer, the term of this patent is extended or adjusted under 35 U.S.C. 154(b) by 40 days.

(21) Appl. No.: 15/211,140

(22) Filed: Jul. 15, 2016

(65) Prior Publication Data

US 2017/0343470 A1 Nov. 30, 2017

(30) Foreign Application Priority Data

May 24, 2016 (CN) .......................... 2016 1 0349317

(51) Int. Cl.
*G01J 3/46* (2006.01)
*G01N 21/25* (2006.01)
*A61B 5/00* (2006.01)
*G01N 33/493* (2006.01)
*G01N 33/49* (2006.01)

(52) U.S. Cl.
CPC .......... *G01N 21/251* (2013.01); *A61B 5/0002* (2013.01); *A61B 5/0022* (2013.01); *G01N 33/49* (2013.01); *G01N 33/493* (2013.01)

(58) Field of Classification Search
CPC .... G01N 21/251; G01N 33/49; G01N 33/493; A61B 5/0002; A61B 5/0022

USPC ......................................................... 356/402
See application file for complete search history.

(56) References Cited

U.S. PATENT DOCUMENTS

| 2011/0275162 A1* | 11/2011 | Xie | G01N 21/78 436/164 |
| 2013/0276521 A1* | 10/2013 | Fuerst | G01N 33/493 73/61.59 |
| 2014/0378777 A1* | 12/2014 | Conrad | A61B 5/0515 600/301 |
| 2015/0335284 A1* | 11/2015 | Nuovo | A61B 5/0022 600/301 |
| 2016/0139156 A1* | 5/2016 | Lakdawala | G01N 21/8483 435/7.92 |

* cited by examiner

*Primary Examiner* — Hina F Ayub
(74) *Attorney, Agent, or Firm* — ScienBiziP, P.C.

(57) ABSTRACT

A wearable device includes a testing portion, the testing portion includes receiving space, a bottom surface defining an opening, an opposite top surface, and a first side surface defining a slot. A white light source is received in the receiving space. A wearable portion of the device is secured to the testing portion and the wearable portion can be placed around a terminal device comprising a camera. The opening faces the camera when the wearable portion is around the terminal device, allowing the camera to capture a standard image of the white light, and capture a wet image of a test paper imbued with user bio-matter when the test paper is inserted into the slot. A biological information of the user, as an indicator of health, is calculated according to a color comparison between the wet image and the standard image.

9 Claims, 3 Drawing Sheets

WEARABLE DEVICE FOR TESTING BIOLOGICAL INFORMATION OF USER AND TESTING SYSTEM HAVING THE SAME

FIELD

The subject matter herein generally relates to wearable devices, and particularly, to a wearable device for testing health of a user and a testing system having the wearable device.

BACKGROUND

As electronic devices have been made smaller, a new class of wearable devices can be configured to be worn by a user which may come in the form of a watch or a bracelet. Additionally, since biological information of a user (for example, an amount of glucose in urine) is a critical parameter for evaluating a state of health of the user, a wearable device capable of testing that is required.

BRIEF DESCRIPTION OF THE DRAWINGS

Implementations of the present technology will now be described, by way of example only, with reference to the attached figures.

DETAILED DESCRIPTION

Figure 1:
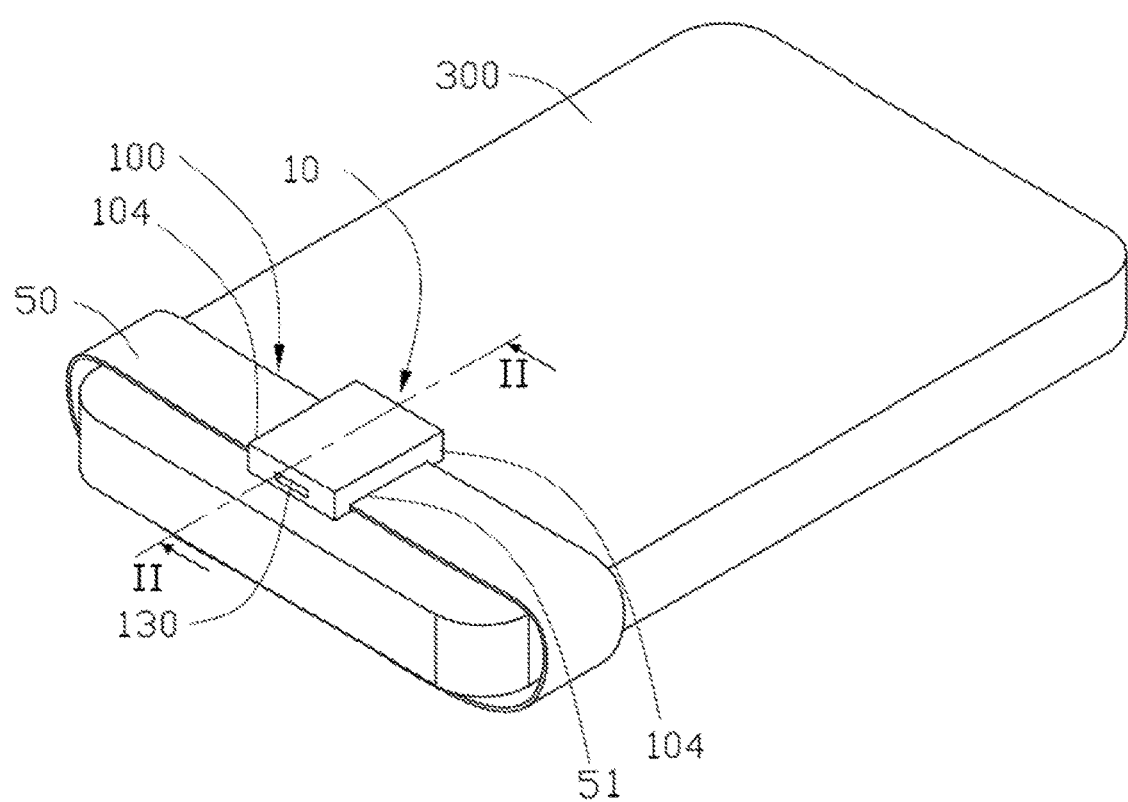
FIG. 1 is a diagrammatic view of a first exemplary embodiment of a testing system including a terminal device and a wearable device placed around the terminal device.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

Several definitions that apply throughout this disclosure will now be presented.

The term "substantially" is defined to be essentially conforming to the particular dimension, shape, or other feature that the term modifies, such that the component need not be exact. For example, "substantially cylindrical" means that the object resembles a cylinder, but can have one or more deviations from a true cylinder. The term "comprising," when utilized, means "including, but not necessarily limited to"; it specifically indicates open-ended inclusion or membership in the so-described combination, group, series, and the like.

Figure 2:
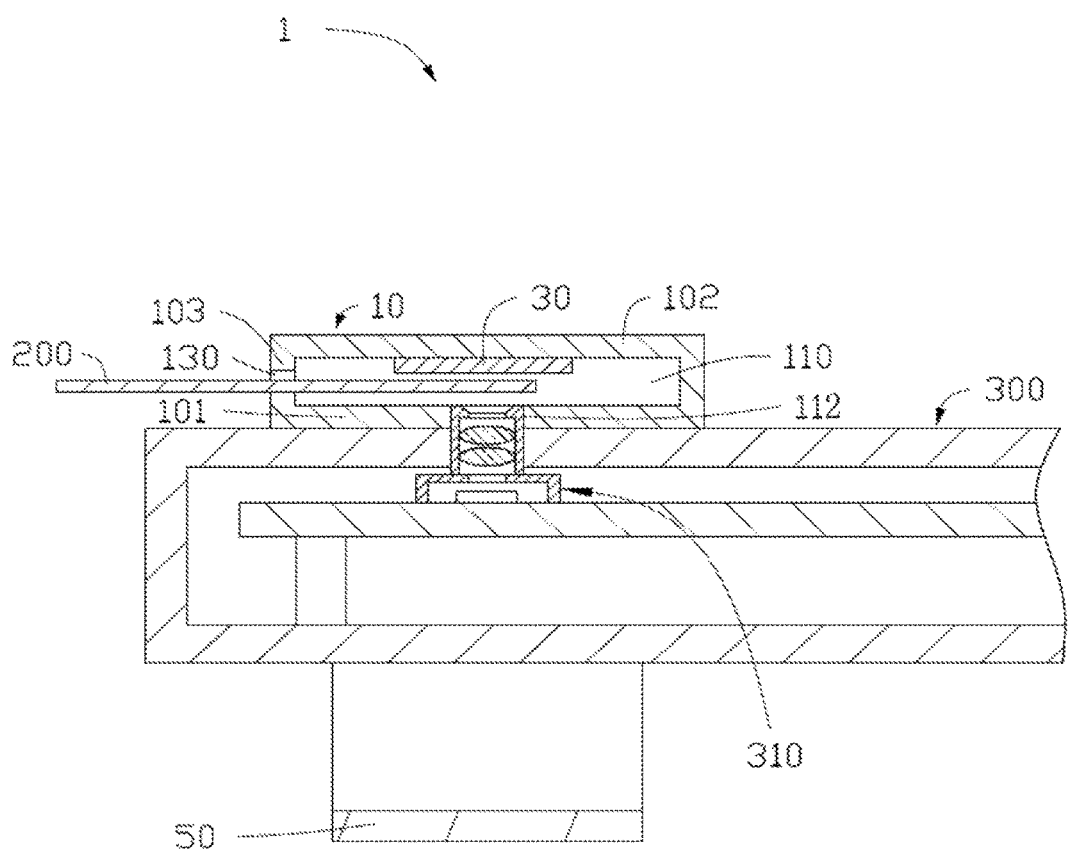
FIG. 2 is a cross-sectional view taken along line II-II of FIG. 1.

FIGS. 1 and 2 illustrate a testing system in a first exemplary embodiment (testing system 1), applied in a wearable device 100 for testing biological information of a user, and a terminal device 300. The testing system 1 is configured to test biological information of the user according to a test paper 200 which is wetted with biologic fluid sample (such as urine or blood) from the user. The biological information is an indicator of health of the user.

The wearable device 100 comprises a testing portion 10 and a wearable portion 50.

The testing portion 10 can be substantially hollow and rectangular and can comprise a receiving space 110. The testing portion 10 further comprises a bottom surface 101, an opposite top surface 102, and a first side surface 103 positioned between and connecting the bottom surface 101 and the top surface 102. The bottom surface 101 defines an opening 112 communicating with the receiving space 110. The first side surface 103 defines a slot 130 communicating with the receiving space 110. The slot 130 is configured to receive the test paper 200. An axis of the slot 130 is substantially perpendicular to an axis of the opening 112. The testing portion 10 further comprises two second side surfaces 104 positioned between and connecting the bottom surface 101 and the top surface 102. The first side surface 103 is positioned between and connects the two second side surfaces 104.

The testing portion 10 further comprises a light source 30 received in the receiving space 110. The light source 30 is secured to the top surface 102 and is aligned with the opening 112. The light source 30 emits white light towards the opening 112. In at least one exemplary embodiment, the testing portion 10 can further comprise a button (not shown) for the user to control the light source 30 to emit light.

The wearable portion 50 comprises two opposite ends 51 secured to the two second side surfaces 104. As such, the wearable portion 50 can be annular and placed around the terminal device 300. In at least one exemplary embodiment, the testing portion 10 is part of a wristband. In another exemplary embodiment, the testing portion 10 is part of an ankle band. The wearable portion 50 is made of flexible material such as rubber.

The terminal device 300 can communicate with a cloud server (not shown) having biological fluid analysis software, and includes a camera 310. In at least one exemplary embodiment, the terminal device 300 can be a smart phone. In an alternative exemplary embodiment, a cloud server is not required and the biological fluid analysis software can be self-contained in the smart phone/terminal device.

When in use, the wearable portion 50 is placed around the terminal device 300 to cause the opening 112 to face the camera 310 of the terminal device 300. In at least one exemplary embodiment, the camera 310 can then capture a number of images of the wearable portion 50. When one captured image comprises the opening 112, the user can determine that the opening 112 faces the camera 310.

The light source 30 emits white light towards the camera 310, thus allowing the camera 310 to capture a standard image of the white light. Then, the test paper 200 wetted with biological fluid sample is inserted into the slot 130, and the test paper 200 is positioned between the camera 310 and the light source 30. The light source 30 is activated again to emit white light, and the camera 310 further captures a wet image of the test paper 200. In one exemplary embodiment, the terminal device 300 sends the standard image and the wet image to the cloud server, which compares the wet images with the standard image. This color comparison allows the cloud server to calculate a bio-information of the user according to the color comparison and using commercially available software or conventional techniques.

Figure 3:
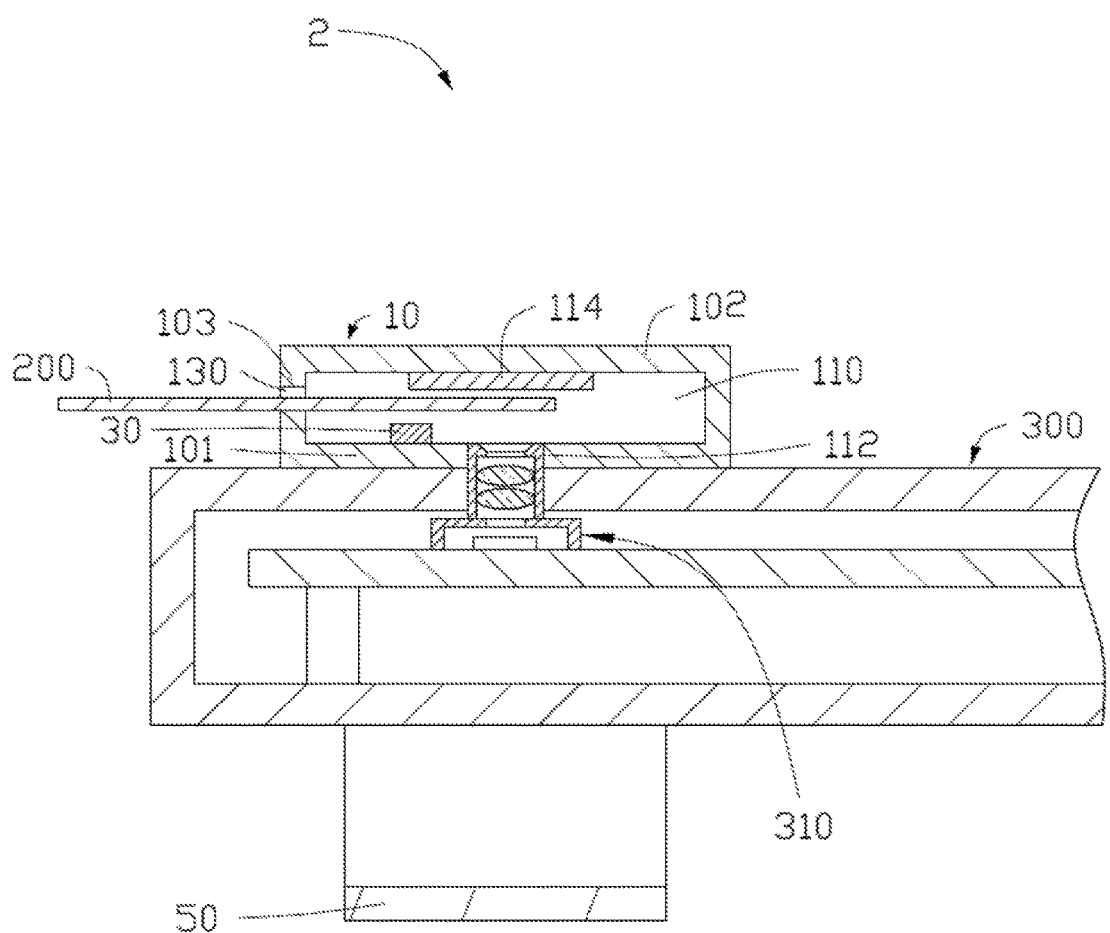
FIG. 3 is similar to FIG. 2 but showing a second exemplary embodiment of a testing system.

FIG. 3 illustrates the testing system 2 of a second exemplary embodiment. The difference from the first exemplary embodiment is that the testing portion 10 further comprises a calibration layer 114 covering the top surface 102. A color of the calibration layer 114 is the same as a color of the test paper 200 before absorbing the biologic fluid sample. The light source 30 is connected to the bottom surface 101, and emits white light towards the calibration layer 114.

In the second exemplary embodiment, when in use, the light source 30 emits white light towards the calibration layer 114, thus allowing the camera 310 to capture an image of the calibration layer 114. At the time of capture, the calibration layer 114 is subject to the white light being radiated from the light source 30, to obtain the standard image. The, the test paper 200 wetted with biological fluid sample is inserted into the slot 130, and the test paper 200 is positioned between the camera 310 and the calibration layer 114. The light source 30 is activated again to emit white light, and the camera 310 further captures the wet image of the test paper 200. Then as described above, the cloud server then compares the wet image with the standard image. This color comparison allows the cloud server to calculate a bio-information of the user according to the color comparison.

Finally, while it is described that a cloud server compares the wet image with the standard image and calculates a bio-information of the user, in an alternative embodiment, a system self-contained within the terminal device 300 can perform the comparison and calculation of the bio-information.

It is to be understood, even though information and advantages of the present exemplary embodiments have been set forth in the foregoing description, together with details of the structures and functions of the present exemplary embodiments, the disclosure is illustrative only; changes may be made in detail, especially in matters of shape, size, and arrangement of parts within the principles of the present exemplary embodiments to the full extent indicated by the plain meaning of the terms in which the appended claims are expressed.

What is claimed is:

1. A testing system for testing a biological information of a user comprising:
    a terminal device comprising a camera;
    a testing portion comprising:
        a receiving space;
        a bottom surface defining an opening communicating with the receiving space;
        a top surface opposite to the bottom surface;
        a first side surface positioned between and connecting the bottom surface and the top surface, and defining a slot communicating with the receiving space, the slot configured to receive a test paper which is wetted with a biologic fluid sample; and
        a light source received in the receiving space and configured to emit white light; and
    a wearable portion secured to the testing portion and configured to be placed around the terminal device;
    wherein the opening faces the camera when the wearable portion is placed around the terminal device, thereby allowing the camera to capture a standard image based on the white light emitted by the light source, and to capture a wet image of the test paper when the test paper is inserted into the slot, the biological information of the user is calculated according to a color comparison between the wet image and the standard image.

2. The testing system of claim 1, wherein the terminal device is configured to send the standard image and the wet image to the cloud server which compares the wet image with the standard image.

3. The testing system of claim 1, wherein the light source is secured to the top surface, aligned with the opening, and configured to emit white light towards the camera when the wearable portion is placed around the terminal device; the standard image is an image of the white light.

4. The testing system of claim 1, wherein the testing portion further comprises a calibration layer covering the top surface; a color of the calibration layer is the same of a color of the test paper before being wetted with the biologic fluid sample; the light source is connected to the bottom surface, and is configured to emit white light towards the calibration layer when the wearable portion is placed around the terminal device; the standard image is an image of the calibration layer under a radiation from the white light.

5. The testing system of claim 1, wherein an axis of the slot is substantially perpendicular to an axis of the opening.

6. The testing system of claim 1, wherein the testing portion further comprises two second side surfaces positioned between and connects the bottom surface and the top surface; the first side surface is positioned between and connects the two second side surfaces; the wearable portion comprises two opposite ends secured to the two second side surfaces, thereby allowing the wearable portion to be annular and placed around the terminal device.

7. The testing system of claim 6, wherein the testing portion is part of a wristband.

8. The testing system of claim 6, wherein the testing portion is part of an ankle band.

9. The testing system of claim 6, wherein the wearable portion is made of flexible material.

* * * * *